(12) United States Patent
Vankov

(10) Patent No.: US 11,020,274 B2
(45) Date of Patent: *Jun. 1, 2021

(54) SUB-NANOSECOND LASER CATARACT SURGERY SYSTEM

(71) Applicant: AMO Development, LLC, Santa Ana, CA (US)

(72) Inventor: Alexander Vankov, Mountain View, CA (US)

(73) Assignee: AMO Development, LLC, Santa Ana, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/359,907

(22) Filed: Mar. 20, 2019

(65) Prior Publication Data

US 2019/0216647 A1  Jul. 18, 2019

Related U.S. Application Data

(63) Continuation of application No. 14/973,508, filed on Dec. 17, 2015, now Pat. No. 10,485,705.
(Continued)

(51) Int. Cl.
*A61F 9/008* (2006.01)
*A61F 9/007* (2006.01)
*A61F 9/009* (2006.01)

(52) U.S. Cl.
CPC .......... *A61F 9/00825* (2013.01); *A61F 9/009* (2013.01); *A61F 9/00736* (2013.01);
(Continued)

(58) Field of Classification Search
CPC .............. A61F 9/00814; A61F 9/00825; A61F 9/00736; A61F 9/00754; A61F 9/009
See application file for complete search history.

(56) References Cited

U.S. PATENT DOCUMENTS

| | | |
|---|---|---|
| 4,538,608 A | 9/1985 | L'Esperance, Jr. |
| 5,480,396 A | 1/1996 | Simon et al. |

(Continued)

FOREIGN PATENT DOCUMENTS

| | | |
|---|---|---|
| AU | 2008323827 B2 | 11/2013 |
| DE | 19702353 C5 | 3/2004 |

(Continued)

OTHER PUBLICATIONS

Duran S., et al., "Erbium:YAG Laser Emulsification of the Cataractous Lens," Journal of Cataract & Refractive Surgery, 2001, vol. 27 (7), pp. 1025-1032.

(Continued)

*Primary Examiner* — Scott Luan
(74) *Attorney, Agent, or Firm* — Johnson & Johnson Surgical Vision, Inc.

(57) ABSTRACT

Systems and methods for fragmenting a lens by a laser cataract surgery system includes a sub-nanosecond laser source generating a treatment beam that includes a plurality of laser beam pulses. An optical delivery system is coupled to the sub-nanosecond laser source to receive and direct the treatment beam. A processor is coupled to the sub-nanosecond laser source and the optical delivery system. The processor includes a tangible non-volatile computer readable medium comprising instructions to determine a lens cut pattern for lens fragmentation and determine a plurality of energies of the treatment beam as a linear function of a depth of the lens cut pattern. The treatment beam is output according to the lens cut pattern and the determined energies.

20 Claims, 5 Drawing Sheets

Related U.S. Application Data

(60) Provisional application No. 62/187,771, filed on Jul. 1, 2015.

(52) U.S. Cl.
CPC ...... *A61F 9/00754* (2013.01); *A61F 9/00814* (2013.01); *A61F 2009/0087* (2013.01); *A61F 2009/00844* (2013.01); *A61F 2009/00851* (2013.01); *A61F 2009/00872* (2013.01); *A61F 2009/00887* (2013.01); *A61F 2009/00889* (2013.01); *A61F 2009/00897* (2013.01)

(56) References Cited

U.S. PATENT DOCUMENTS

| | | | |
|---|---|---|---|
| 5,657,138 A * | 8/1997 | Lewis | B23K 26/032 219/121.73 |
| 5,720,894 A | 2/1998 | Neev et al. | |
| 5,957,915 A | 9/1999 | Trost | |
| 5,984,916 A | 11/1999 | Lai | |
| 6,019,472 A | 2/2000 | Koester et al. | |
| 6,391,020 B1 | 5/2002 | Kurtz et al. | |
| 6,454,761 B1 | 9/2002 | Freedman | |
| 7,008,415 B2 | 3/2006 | Yee et al. | |
| 7,655,002 B2 | 2/2010 | Myers et al. | |
| 7,717,907 B2 | 5/2010 | Ruiz et al. | |
| 8,262,646 B2 | 9/2012 | Frey et al. | |
| 8,350,183 B2 | 1/2013 | Vogel et al. | |
| 8,382,745 B2 | 2/2013 | Naranjo-Tackman et al. | |
| 8,414,564 B2 | 4/2013 | Goldshleger et al. | |
| 8,475,438 B2 | 7/2013 | Larsen | |
| 8,709,001 B2 | 4/2014 | Blumenkranz et al. | |
| 8,758,332 B2 | 6/2014 | Frey et al. | |
| 2002/0013574 A1 | 1/2002 | Elbrecht et al. | |
| 2003/0142703 A1 | 7/2003 | Gao et al. | |
| 2009/0137991 A1 | 5/2009 | Kurtz | |
| 2009/0171327 A1 | 7/2009 | Kurtz et al. | |
| 2009/0177189 A1 | 7/2009 | Raksi | |
| 2010/0191230 A1 | 7/2010 | Dick et al. | |
| 2011/0172649 A1 | 7/2011 | Schuele et al. | |
| 2011/0178512 A1 | 7/2011 | Blumenkranz et al. | |
| 2011/0184395 A1 | 7/2011 | Schuele et al. | |
| 2011/0196350 A1 | 8/2011 | Friedman et al. | |
| 2011/0319873 A1 | 12/2011 | Raksi et al. | |
| 2011/0319875 A1 | 12/2011 | Loesel et al. | |
| 2012/0016350 A1 | 1/2012 | Myers et al. | |
| 2012/0089134 A1 | 4/2012 | Horvath et al. | |
| 2012/0259321 A1 | 10/2012 | Vera et al. | |
| 2012/0296319 A1 | 11/2012 | Chaudhary et al. | |
| 2012/0316544 A1 | 12/2012 | Horvath et al. | |
| 2013/0103013 A1 | 4/2013 | Esposito | |
| 2013/0158530 A1 | 6/2013 | Goldshleger et al. | |
| 2013/0338648 A1 | 12/2013 | Hanebuchi et al. | |
| 2014/0114297 A1 | 4/2014 | Woodley et al. | |
| 2014/0128821 A1 | 5/2014 | Gooding et al. | |
| 2014/0128853 A1 * | 5/2014 | Angeley | A61F 9/00827 606/4 |
| 2014/0135749 A1 | 5/2014 | Goh et al. | |
| 2014/0163534 A1 | 6/2014 | Angeley et al. | |
| 2014/0194860 A1 | 7/2014 | Dick et al. | |
| 2014/0200563 A1 | 7/2014 | Fu et al. | |
| 2014/0276680 A1 | 9/2014 | Dennison et al. | |
| 2014/0316389 A1 | 10/2014 | Schuele et al. | |
| 2015/0342678 A1 * | 12/2015 | Deladurantaye | G01N 33/5005 606/2.5 |

FOREIGN PATENT DOCUMENTS

| | | |
|---|---|---|
| EP | 2574318 A1 | 4/2013 |
| WO | 9308677 A2 | 5/1993 |
| WO | 2011085274 A1 | 7/2011 |
| WO | 2014032678 A1 | 3/2014 |

OTHER PUBLICATIONS

International Search Report and Written Opinion for Application No. PCT/US2015/066499, dated Mar. 14, 2016, 14 pages.
International Search Report and Written Opinion for Application No. PCT/US2016/037700, dated Oct. 18, 2016, 16 pages.
Mastropasqua L., et al., "Scanning Electron Microscopy Evaluation of Capsulorhexis in Femtosecond Laser—Assisted Cataract Surgery," Journal of Cataract & Refractive Surgery, 2013, vol. 39 (10), pp. 1581-1586.
Palanker D.V., et al., "Femtosecond Laser-Assisted Cataract Surgery with Integrated Optical Coherence Tomography," Science Translational Medicine, 2010, vol. 2 (58), pp. 58ra85.
Partial International Search Report for Applicaiton No. PCT/US2016/037700, dated Aug. 25, 2016, 6 pages.
Wetzel W., et al., "Photofragmentation of Lens Nuclei Using the Er:YAG laser: Preliminary Report of an in Vitro Study," German Journal of Ophthalmology, 1996, vol. 5 (5), pp. 281-284.

* cited by examiner

SUB-NANOSECOND LASER CATARACT SURGERY SYSTEM

CROSS-REFERENCE TO RELATED APPLICATIONS

This application is a continuation of U.S. patent application Ser. No. 14/973,508, filed Dec. 17, 2015, which is a non-provisional application and claims the benefit under 35 U.S.C. § 119(e) of U.S. Provisional Application Ser. No. 62/187,771, filed Jul. 1, 2015. The above-referenced applications are incorporated herein in their entireties by reference.

BACKGROUND

The present disclosure relates generally to tissue cutting induced by a pulsed laser beam and the energy of the pulsed laser beam. Although specific reference is made to cutting tissue for surgery such as cataract surgery, embodiments as described herein can be used in many ways with many materials to treat one or more of many materials, such as cutting of optically transparent materials.

Cutting of materials can be done mechanically with chisels, knives, scalpels and other tools such as surgical tools. Pulsed lasers can be used to cut one or more of many materials and have been used for laser surgery to cut tissue. However, prior methods and apparatus of cutting can be less than desirable in at least some instances. For example, at least some prior methods and apparatus for cutting materials such as tissue are unsuitable due to their cost and size.

Cataract extraction is one of the most commonly performed surgical procedures in the world. A cataract is formed by opacification of the crystalline lens or its envelope (the lens capsule) of the eye. The cataract obstructs passage of light through the lens. A cataract can vary in degree from slight to complete opacity. Early in the development of an age-related cataract the power of the lens may be increased, causing near-sightedness (myopia). Gradual yellowing and opacification of the lens may reduce the perception of blue colors as those wavelengths are absorbed and scattered within the crystalline lens. Cataract formation typically progresses slowly resulting in progressive vision loss. Cataracts are potentially blinding if untreated.

A common cataract treatment involves replacing the opaque crystalline lens with an artificial intraocular lens (IOL). Presently, an estimated 15 million cataract surgeries per year are performed worldwide. The cataract treatment market is composed of various segments including intraocular lenses for implantation, viscoelastic polymers to facilitate surgical procedures, and disposable instrumentation including ultrasonic phacoemulsification tips, tubing, various knives, and forceps.

Presently, cataract surgery is typically performed using a technique termed phacoemulsification in which an ultrasonic tip with associated irrigation and aspiration ports is used to sculpt the relatively hard nucleus of the lens to facilitate removal through an opening made in the anterior lens capsule. The nucleus of the lens is contained within an outer membrane of the lens that is referred to as the lens capsule. Access to the lens nucleus can be provided by performing an anterior capsulotomy in which a small (often round) hole is formed in the anterior side of the lens capsule through which the surgeon excises the whole lens. Access to the lens can also be provided by performing a manual continuous curvilinear capsulorhexis (CCC) procedure. The lens may then be fragmented by segmenting and/or softening the lens by a femtosecond laser to aid in removal by a phacoemulsification tip. Removal of the lens with the phacoemulsification tip is then performed through a primary corneal incision, for instance. After removal of the lens nucleus, a synthetic foldable intraocular lens (IOL) can be inserted into the remaining lens capsule of the eye.

Prior methods and apparatuses to incise tissue with laser beams can be less than ideal in at least some instances. For example, femtosecond laser cutting systems are used in performing lens fragmentation. Femtosecond laser technology provides a short duration (e.g., approximately $10^{-13}$ seconds in duration) laser pulse (with energy level in the micro joule range) that can be delivered to a tightly focused point to disrupt tissue. Femtosecond lasers are well-suited for providing clean cuts in a lens through a relatively wide range of energy levels. However, the high cost and large size of femtosecond laser cutting systems prevent those systems from more widespread usage.

Infrared laser cutting systems, such as picosecond lasers, are smaller and more cost-effective relative to femtosecond laser cutting systems, but are not used for lens fragmentation. These systems provide cuts to a nucleus of the lens with energy level in the tens of micro joule range that are coarser than the cuts provided by a femtosecond laser beam. The quality of the cuts are poor and non-uniform throughout the lens, resulting in defects such as patching, incomplete cuts and excess damage from large bubbles generated by the laser. Examples of incomplete cutting includes bridging where two cut portions remain connected together, thereby complicating subsequent nucleus removal. Excess damage to the tissue creates lamella separation that crack the lens and block subsequent laser pulses. Therefore, further laser cutting is not possible once a lens is delaminated. Although infrared laser systems are attractive from a cost perspective, these performance deficiencies have prevented their use for lens fragmentation.

Thus, improved methods and systems for lens fragmentation and treating cataracts are needed. In light of the above, it would be desirable to have improved methods and apparatus of treating materials with laser beams, such as the surgical cutting of tissue to treat cataracts with cost effective surgical systems. At least some of the above deficiencies of the prior methods and apparatus are overcome by the embodiments described herein.

SUMMARY

Improved laser eye surgery systems, and related methods, are provided. The laser eye surgery systems use a laser to form precise incisions in the crystalline lens nucleus. Although specific reference is made to tissue cutting for laser eye surgery, embodiments as described herein can be used in one or more of many ways with many surgical procedures and devices, such as orthopedic surgery, robotic surgery and microkeratomes.

Thus, in one aspect, a laser cataract surgery system is provided and may include a sub-nanosecond laser source generating a treatment beam that includes a plurality of laser beam pulses. An optical delivery system may be coupled to the sub-nanosecond laser source to receive and direct the treatment beam. A processor may be coupled to the sub-nanosecond laser source and the optical delivery system. The processor includes a tangible non-volatile computer readable medium including instructions to determine a lens cut pattern for lens fragmentation and determine a plurality of energies of the treatment beam as a linear function of a depth of the lens cut pattern. The treatment beam may be output according to the lens cut pattern and the determined energies.

In some embodiments, the plurality of energies of the treatment beam may be between twice an energy threshold and ten times an energy threshold. The energy threshold is an energy level at which visible damage in tissue is first observed. In some variations, the sub-nanosecond laser source generates the treatment beam with an energy five times the energy threshold of the tissue. The sub-nanosecond laser source may be a picosecond laser. The sub-nanosecond laser may generate a 150 picosecond treatment beam.

In some variations, the laser system may include an image capture system for capturing an image of the eye. A patient interface system may couple the eye with the optical delivery system so as to constrain the eye relative to the optical delivery system.

In some embodiments, a method of fragmenting a lens is provided and includes the steps of determining a lens cut pattern for lens fragmentation. A treatment beam may be generated that includes a plurality of laser beam pulses by a sub-nanosecond laser source. A plurality of energies of the treatment beam may be determined as a linear function of a depth of the lens cut pattern. The treatment beam may be output according to the lens cut pattern and the determined energies.

In some variations, the plurality of energies of the treatment beam are between twice an energy threshold and ten times an energy threshold. The energy threshold may be an energy level at which visible damage in tissue is first observed. The sub-nanosecond laser source may generate the treatment beam with an energy five times the energy threshold of the tissue. The sub-nanosecond laser source may be a picosecond laser. The sub-nanosecond laser may generate a 150 picosecond treatment beam.

In other variations, an image of the eye may be captured by an image capture system. The eye may be coupled with the optical delivery system so as to constrain the eye relative to the optical delivery system by a patient interface system.

Variations of the laser eye surgery system are provided. For example, a laser cataract surgery system includes a sub-nanosecond laser source generating a treatment beam that includes a plurality of laser beam pulses. An optical delivery system may be coupled to the sub-nanosecond laser source to receive and direct the treatment beam. A processor may be coupled to the sub-nanosecond laser source and the optical delivery system. The processor may include a tangible non-volatile computer readable medium including instructions to determine a lens cut pattern from a posterior to an anterior of the lens for lens fragmentation. A plurality of energies of the treatment beam may be scaled as a function of a depth of the lens cut pattern to maintain a bubble volume formed by the single pulse of treatment beam. The treatment beam may be output according to the lens cut pattern and the determined energies.

In some variations, the plurality of energies may be scaled linearly with a depth of the lens cut pattern. The energy of the treatment beam may decrease as a function of the depth of the lens linearly from the posterior to the anterior of the lens. The energy of the treatment beam at the posterior of the lens may be between twice an energy threshold and ten times an energy threshold. The energy threshold may be an energy level at which visible damage in tissue is first observed.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
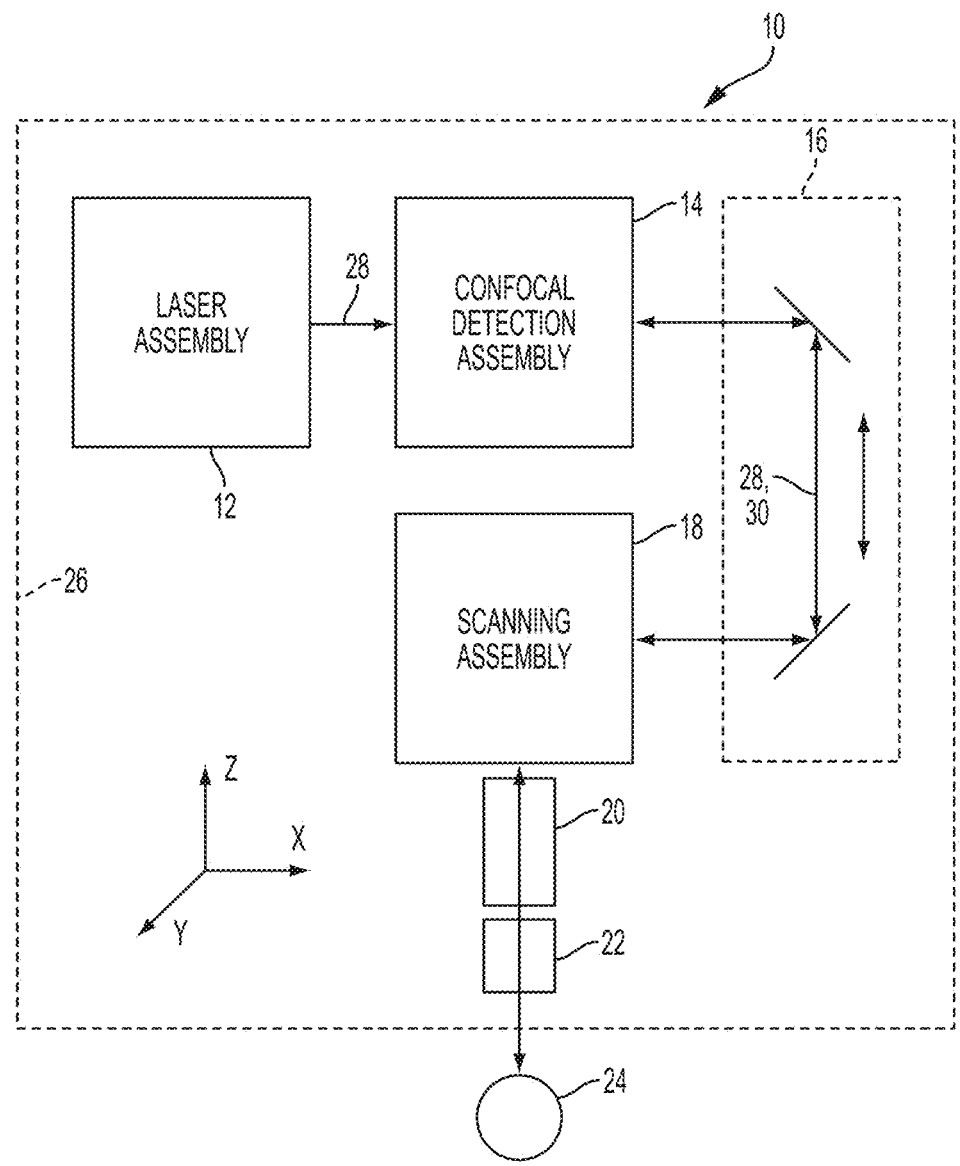
FIG. 1 is a schematic diagram of a laser surgery system, in accordance with many embodiments.

Methods and systems related to laser eye surgery are disclosed. A laser is used to form precise incisions in the cornea, in the lens capsule, and/or in the crystalline lens nucleus. In many embodiments, a laser eye surgery system includes a laser source to produce a laser pulse treatment beam to incise tissue within the eye, an imaging system to measure the spatial disposition of external and internal structures of the eye in which incisions can be formed, a scanning assembly operable to scan the treatment beam, and can include a video subsystem that can be used to, for example, provide images of the eye during docking of the eye to the laser eye surgery system and also provide images of the eye once the docking process is complete. In many embodiments, a liquid interface is used between a patient interface lens and the eye. The use of the liquid interface avoids imparting undesirable forces to the patient's eye.

The embodiments as described herein are particularly well suited for treating tissue, such as with the surgical treatment of tissue. In many embodiments, the tissue comprises an optically transmissive tissue, such as tissue of an eye. The embodiments as described herein can be particularly well suited for increasing the quality of the cutting of the material such as tissue, for example.

As used herein, like characters such as reference numerals and letters describe like elements. As used herein, the terms anterior and posterior refers to known orientations with respect to the patient. An energy threshold is used herein to mean an energy level of laser beam pulses that cause the first visible damage in tissue. Photodisruption is generally used for the first visible damage in tissue by a UV laser.

Depending on the orientation of the patient for surgery, the terms anterior and posterior may be similar to the terms upper and lower, respectively, such as when the patient is placed in a supine position on a bed. The terms distal and anterior may refer to an orientation of a structure from the perspective of the user, such that the terms proximal and distal may be similar to the terms anterior and posterior when referring to a structure placed on the eye, for example. A person of ordinary skill in the art will recognize many variations of the orientation of the methods and apparatus as described herein, and the terms anterior, posterior, proximal, distal, upper, and lower are used merely by way of example.

FIG. 1 schematically illustrates a laser surgery system 10, according to many embodiments. The laser surgery system 10 may include a laser source/assembly 12, a confocal detection assembly 14, a free-floating mechanism 16, a scanning assembly 18, an objective lens assembly 20, and a patient interface device 22. The patient interface device 22 may be configured to interface with a patient 24. The patient interface device 22 may be supported by the objective lens assembly 20, which may be supported by the scanning assembly 18, which may be supported by the free-floating mechanism 16. The free-floating mechanism 16 may have a portion having a fixed position and orientation relative to the laser assembly 12 and the confocal detection assembly 14. An optical delivery system for receiving and directing the treatment beam may comprise some or all of the components coupled to the to the sub-nanosecond laser assembly 12.

In some embodiments, the patient interface device 22 can be configured to be coupled to an eye of the patient 24 using vacuum as described in co-pending U.S. patent application Ser. No. 14/068,994, entitled "Liquid Optical Interface for Laser Eye Surgery System," filed Oct. 31, 2013, the entire disclosure of which is incorporated herein by reference. The laser surgery system 10 can further optionally include a base assembly 26 that can be fixed in place or be repositionable. For example, the base assembly 26 can be supported by a support linkage that is configured to allow selective repositioning of the base assembly 26 relative to a patient and/or securing the base assembly 26 in a selected fixed position relative to the patient. Such a support linkage can be a fixed support base or a movable cart that can be repositioned to a suitable location adjacent to a patient. In many embodiments, the support linkage includes setup joints with each setup joint being configured to permit selective articulation of the setup joint, and can be selectively locked to prevent inadvertent articulation of the setup joint, thereby securing the base assembly 26 in a selected fixed position relative to the patient when the setup joints are locked.

In many embodiments, the laser assembly 12 may be configured to emit an electromagnetic radiation beam 28. The beam 28 can include a series of laser pulses of any suitable energy level, duration, and repetition rate. In many embodiments, the laser assembly 12 incorporates sub-nanosecond laser technology where a short duration (e.g., approximately 10 ns to 1 picosecond in duration) laser pulse (with energy level in the tens of micro joules range) can be delivered to a tightly focused point to disrupt tissue, thereby substantially lowering the energy level required to image and/or modify an intraocular target as compared to laser pulses having longer durations. The laser assembly 12 may produce laser pulses having a wavelength suitable to treat and/or image tissue. For example, the laser assembly 12 can be configured to emit an electromagnetic radiation beam 28 such as that emitted by any of the laser surgery systems described in co-pending U.S. patent application Ser. No. 14/069,044, entitled "Laser Eye Surgery System," filed Oct. 31, 2013, and U.S. patent application Ser. No. 12/987,069, entitled "Method and System For Modifying Eye Tissue and Intraocular Lenses," filed Jan. 7, 2011, the fill disclosures of which are incorporated herein by reference.

In some embodiments, the laser assembly may produce laser pulses having a wavelength of 355 nm with a numerical aperture NA in the range of 0.05 to 0.40, and preferably 0.15. The pulse length may be 0.6 ns with a pulse rate of 1 kHz to 1 mHz, and preferably 70 kHz to 100 kHz. Spot spacing may be from 6 µm to 40 µm.

The selection of NA may be based upon laser power, pulse rate, cut time, as well as safe incidental exposure levels of the iris and other ocular tissues not targeted by the cut. For instance, as the NA decreases, the laser power required increases. Also, the time needed for a cut of unit area ($mm^2$) increases with increasing NA due to lower threshold energies. Therefore, increased NA tends to lead to an increased number of pulses and longer cut times.

In other varying embodiments, the laser assembly 12 may produce laser pulses having a wavelength between 800 nm to 1200 nm, and preferably between 1020 nm to 1050 nm. The pulse duration of the laser light can vary from 1 ps to 1000 ps. The pulse repetition frequency can also vary from 10 kHz to 500 kHz. Safety limits with regard to unintended damage to non-targeted tissue bound the upper limit with regard to repetition rate and pulse energy. Threshold energy, time to complete the procedure, and stability can bound the lower limit for pulse energy and repetition rate. The peak power of the focused spot in the eye 24 and specifically within the crystalline lens and the lens capsule of the eye is sufficient to produce optical breakdown and initiate visible damage in tissue. In yet another embodiment, the laser assembly 12 may have a diode-pumped solid-state configuration with a 1030 (+/−5) nm center wavelength. The laser assembly 12 can also include two or more lasers of any suitable configuration.

The laser assembly 12 may include control and conditioning components. In an embodiment, the control components may include a beam attenuator to control the energy of the laser pulse and the average power of the pulse train, a fixed aperture to control the cross-sectional spatial extent of the beam containing the laser pulses, one or more power monitors to monitor the flux and repetition rate of the beam train and therefore the energy of the laser pulses, and a shutter to allow/block transmission of the laser pulses. The conditioning components may include an adjustable zoom assembly and a fixed optical relay to transfer the laser pulses over a distance while accommodating laser pulse beam positional and/or directional variability, thereby providing increased tolerance for component variation.

In many embodiments, the laser assembly 12 and the confocal detection assembly 14 may have fixed positions relative to the base assembly 26. The beam 28 emitted by the laser assembly 12 may propagate along a fixed optical path through the confocal detection assembly 14 to the free-floating mechanism 16. The beam 28 may propagate through the free-floating mechanism 16 along a variable optical path 30, which may deliver the beam 28 to the scanning assembly 18. In many embodiments, the beam 28 emitted by the laser assembly 12 may be collimated so that the beam 28 is not impacted by patient movement-induced changes in the length of the optical path between the laser assembly 12 and the scanner 18. The scanning assembly 18 may be operable to scan the beam 28 (e.g., via controlled variable deflection of the beam 28) in at least one dimension. In many embodiments, the scanning assembly 18 is operable to scan the beam 28 in two dimensions transverse to the direction of propagation of the beam 28 and may be further operable to scan the location of a focal point of the beam 28 in the direction of propagation of the beam 28. The scanned beam may be emitted from the scanning assembly 18 to propagate through the objective lens assembly 20, through the interface device 22, and to the patient 24.

The free-floating mechanism 16 may be configured to accommodate a range of movement of the patient 24 relative to the laser assembly 12 and the confocal detection assembly 14 in one or more directions while maintaining alignment of the beam 28 emitted by the scanning assembly 18 with the patient 24. For example, the free-floating mechanism 16 may be configured to accommodate a range movement of the patient 24 in any direction defined by any combination of unit orthogonal directions (X, Y, and Z).

In some embodiments, the scanning assembly 18 can include a Z-scan device and an XY-scan device. The laser surgery system 10 may be configured to focus the electromagnetic radiation beam 28 to a focal point that is scanned in three dimensions. The Z-scan device may be operable to vary the location of the focal point in the direction of propagation of the beam 28. The XY-scan device may be operable to scan the location of the focal point in two dimensions transverse to the direction of propagation of the beam 28. Accordingly, the combination of the Z-scan device and the XY-scan device can be operated to controllably scan the focal point of the beam in three dimensions, including: within a tissue, e.g., eye tissue, of the patient 24. The scanning assembly 18 may be supported by the free-floating mechanism 16, which may accommodate patient movement, induced movement of the scanning assembly 18 relative to the laser assembly 12 and the confocal detection assembly 14 in three dimensions.

Because the patient interface device 22 may be interfaced with the patient 24, movement of the patient 24 may result in corresponding movement of the patient interface device 22, the objective lens assembly 20, and the scanning assembly 18. The free-floating mechanism 16 can include, for example, any suitable combination of a linkage that accommodates relative movement between the scanning assembly 18 and, for example, the confocal detection assembly 14, and optical components suitably coupled to the linkage so as to form the variable optical path 30. In an embodiment, the free-floating mechanism 16 can be configured as described in U.S. patent application Ser. No. 14/191,095 and PCT Application No. PCT/US2014/018752, filed Feb. 26, 2014 and entitled "Laser Surgery System," the entire disclosures of which are incorporated herein by reference.

A portion of electromagnetic radiation beam 28 may reflect from an eye tissue at the focal point and may propagate back to the confocal detection assembly 14. Specifically, a reflected portion of the electromagnetic radiation beam 28 may travel back through the patient interface device 22, back through the objective lens assembly 20, back through (and de-scanned by) the scanning assembly 18, back through the free-floating mechanism 16 (along the variable optical path 30), and to the confocal detection assembly 14. In many embodiments, the reflected portion of the electromagnetic radiation beam that travels back to the confocal detection assembly 14 may be directed to be incident upon a sensor that generates an intensity signal indicative of intensity of the incident portion of the electromagnetic radiation beam. The intensity signal, coupled with associated scanning of the focal point within the eye, can be processed in conjunction with the parameters of the scanning to, for example, image/locate structures of the eye, such as the anterior surface of the cornea, the posterior surface of the cornea, the iris, the anterior surface of the lens capsule, the posterior surface of the lens capsule, and so on. In many embodiments, the amount of the reflected electromagnetic radiation beam that travels to the confocal detection assembly 14 may be substantially independent of expected variations in the length of the variable optical path 30 due to patient movement, thereby enabling the ability to ignore patient movements when processing the intensity signal to image/locate structures of the eye.

The confocal detection assembly 14 may comprise a confocal imaging system which operates at the same wavelength as the electromagnetic radiation beam. The confocal imaging system combined with an inexpensive sub-nanosecond laser provides a cost effective and compact surgical system.

In many embodiments, the system 10 includes external communication connections. For example, the system 10 can include a network connection (e.g., an RJ45 network connection) for connecting the system 10 to a network. The network connection can be used to enable network printing of treatment reports, remote access to view system performance logs, and remote access to perform system diagnostics. The system 10 can include a video output port (e.g., HDMI) that can be used to output video of treatments performed by the system 10. The output video can be displayed on an external monitor for, for example, viewing and/or training. The output video can also be recorded for, for example, archival purposes. The system 10 can include one or more data output ports (e.g., USB) to, for example, enable export of treatment reports to a data storage device. The treatments reports stored on the data storage device can then be accessed at a later time for any suitable purpose such as, for example, printing from an external computer in the case where the user without access to network based printing.

Figure 2:
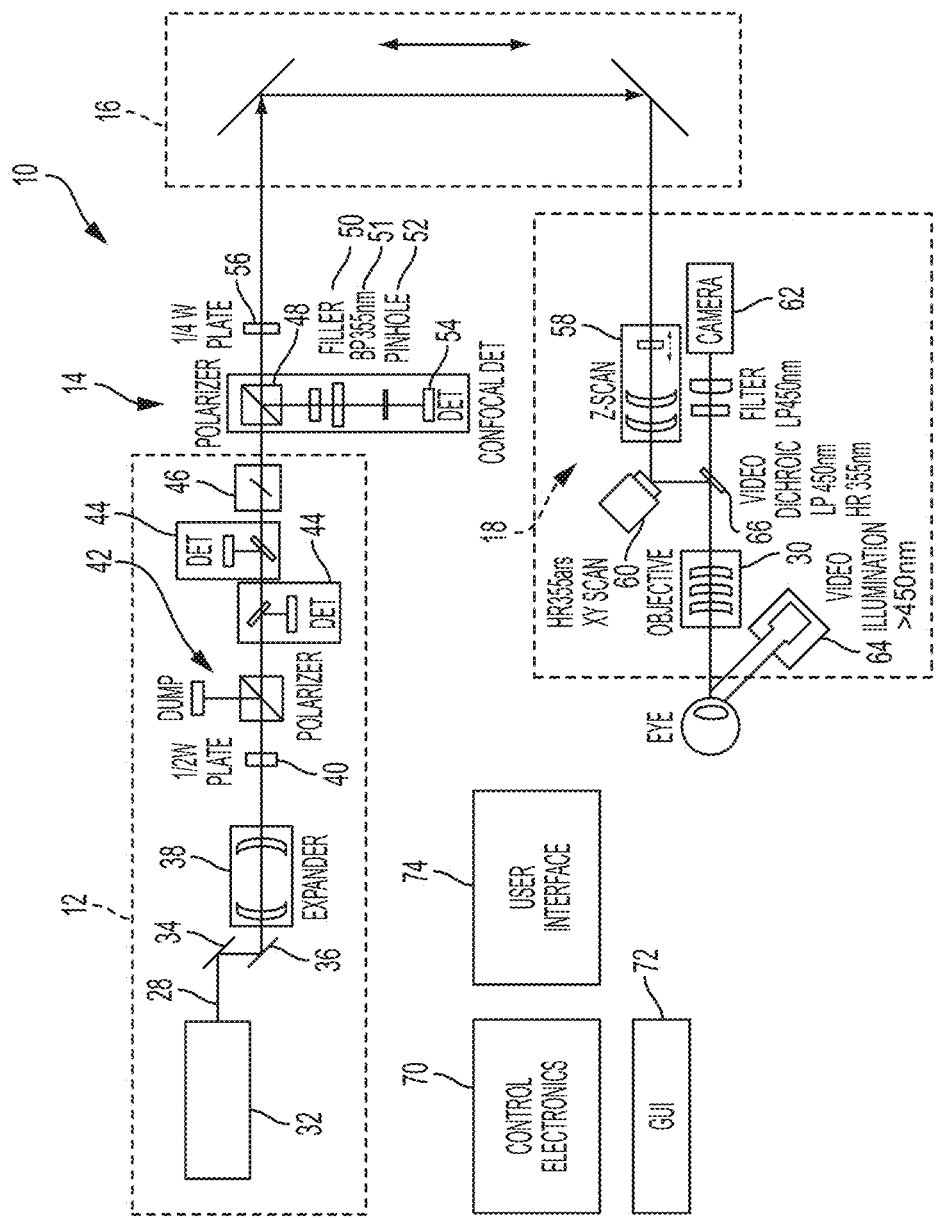
FIG. 2 is a schematic diagram of the laser surgery system of FIG. 1, in accordance with many embodiments.

FIG. 2 schematically illustrates details of an embodiment of the laser surgery system 10. Specifically, example configurations are schematically illustrated for the laser assembly 12, the confocal detection assembly 14, and the scanning assembly 18. As shown in the illustrated embodiment, the laser assembly 12 may include an IR laser 32, alignment mirrors 34, 36, a beam expander 38, a one-half wave plate 40, a polarizer and beam dump device 42, output pickoffs and monitors 44, and a system-controlled shutter 46. The electromagnetic radiation beam 28 output by the laser 32 may be deflected by the alignment mirrors 34, 36. In many embodiments, the alignment mirrors 34, 36 may be adjustable in position and/or orientation so as to provide the ability to align the beam 28 with the downstream optical path through the downstream optical components. Next, the beam 28 may pass through the beam expander 38, which can increase the diameter of the beam 28. The expanded beam 28 may then pass through the one-half wave plate 40 before passing through the polarizer 42. The beam exiting the polarizer 42 may be linearly polarized. The one-half wave plate 40 can rotate this polarization. The amount of light passing through the polarizer 42 depends on the angle of the rotation of the linear polarization. Therefore, the one-half wave plate 40 with the polarizer 42 may act as an attenuator of the beam 28. The light rejected from this attenuation may be directed into the beam dump. Next, the attenuated beam 28 may pass through the output pickoffs and monitors 44 and then through the system-controlled shutter 46. By locating the system-controlled shutter 46 downstream of the output pickoffs and monitors 44, the power of the beam 28 can be checked before opening the system-controlled shutter 46.

The system 10 can be set to locate the anterior and posterior surfaces of the lens capsule and cornea and ensure that the laser pulse beam 28 will be focused on the lens capsule and cornea at all points of the desired opening. In the embodiment of FIGS. 1 and 2, a confocal detection assembly 14 is described, although other modalities are within the scope of the present invention. Imaging modalities and techniques described herein, such as for example, Optical Coherence Tomography (OCT), Purkinje imaging, Scheimpflug imaging, structured light illumination, confocal backreflectance imaging, fluorescence imaging, or ultrasound may be used to determine the location and measure the thickness of the lens and lens capsule to provide greater precision to the laser focusing methods, including 2D and 3D patterning, or other known ophthalmic or medical imaging modalities and/or combinations thereof. An OCT scan of the eye will provide information about the axial location of the anterior and posterior lens capsule, the boundaries of the cataract nucleus, as well as the depth of the anterior chamber. This information is then be loaded into the control electronics 70, and used to program and control the subsequent laser-assisted surgical procedure. The information may also be used to determine a wide variety of parameters related to the procedure such as, for example, the upper and lower axial limits of the focal planes used for modifying the lens capsule, cornea, and synthetic intraocular lens implant, among others.

For instance, an optical coherence tomography (OCT) system may be used in place of the confocal imaging system. The OCT system is configured to produce a source beam used to locate one or more structures of the eye, such as by measuring the spatial disposition of eye structures in three dimensions. The measured eye structures can include the anterior and posterior surfaces of the cornea, the anterior and posterior portions of the lens capsule, the iris, and the limbus. As a non-limiting example, the system 10 can be configured to use an OCT imaging system employing wavelengths from 780 nm to 970 nm, or more particularly, from 810 nm to 850 nm. Such an OCT imaging system can employ a reference path length that is adjustable to adjust the effective depth in the eye of the OCT measurement, thereby allowing the measurement of system components including features of the patient interface that lie anterior to the cornea of the eye and structures of the eye that range in depth from the anterior surface of the cornea to the posterior portion of the lens capsule and beyond.

As shown in the illustrated embodiment, the scanning assembly 18 may include a Z-scan device 58 and an XY-scan device 60. The Z-scan device 58 may be operable to vary a convergence/divergence angle of the beam 28 and thereby change a location of the focal point in the direction of propagation of the beam 28. For example, the Z-scan device 58 may include one or more lenses that are controllably movable in the direction of propagation of the beam 28 to vary a convergence/divergence angle of the beam 28. The XY-scan device 60 may be operable to deflect the beam 28 in two dimensions transverse to the direction of propagation of the beam 28. For example, the XY-scan device 60 can include one or more mirrors that are controllably deflectable to scan the beam 28 in two dimensions transverse to the direction of propagation of the beam 28. Accordingly, the combination of the z-scan device 58 and the xy-scan device 60 can be operated to controllably scan the focal point in three dimensions, for example, within the eye of the patient.

As shown further in the illustrated embodiment, a camera 62 and associated video illumination 64 can be integrated with the scanning assembly 18. The camera 62 and the beam 28 may share a common optical path through the objective lens assembly 20 to the eye. A video dichroic 66 may be used to combine/separate the beam 28 with/from the illumination wavelengths used by the camera. For example, the beam 28 can have a wavelength of about 355 nm and the video illumination 64 can be configured to emit illumination having wavelengths greater than 450 nm. Accordingly, the video dichroic 66 can be configured to reflect the 355 nm wavelength while transmitting wavelengths greater than 450 nm.

As should be appreciated, the laser surgery system 10 scans the eye with focal points of more than one electromagnetic radiation beam, where the electromagnetic radiation beams have varying degrees of polarization due to a varying wave plate orientation. The plurality of scans may compensate for imaging signal loss due to local cornea birefringence properties.

The system 10 can include control and conditioning components. For example, such control components can include components such as a beam attenuator to control the energy of the laser pulse and the average power of the pulse train, a fixed aperture to control the cross-sectional spatial extent of the beam containing the laser pulses, one or more power monitors to monitor the flux and repetition rate of the beam train and therefore the energy of the laser pulses, and a shutter to allow/block transmission of the laser pulses. Such conditioning components can include an adjustable zoom assembly to adapt the beam containing the laser pulses to the characteristics of the system 10 and a fixed optical relay to transfer the laser pulses over a distance while accommodating laser pulse beam positional and/or directional variability, thereby providing increased tolerance for component variation.

The control electronics 70 controls the operation of and can receive input from the laser assembly 12, the confocal detection assembly 14, free-floating mechanism 16, the scanning assembly 18, the objective lens assembly 20, the patient interface 22, control panel/graphical user interface (GUI) 72, and user interface devices 74 via communication paths. The communication paths can be implemented in any suitable configuration, including any suitable shared or dedicated communication paths between the control electronics 70 and the respective system components.

The control electronics 70 can include any suitable components, such as one or more processors, one or more field-programmable gate array (FPGA), and one or more memory storage devices. The control electronics 70 is operatively coupled via the communication paths with the laser assembly 12, the confocal detection assembly 14, the free-floating mechanism 16, the scanning assembly 18, the control panel/GUI 72, and the user interface devices 74. In many embodiments, the control electronics 70 controls the control panel/GUI 72 to provide for pre-procedure planning according to user specified treatment parameters as well as to provide user control over the laser eye surgery procedure.

The control electronics 70 can include a processor/controller that is used to perform calculations related to system operation and provide control signals to the various system elements. A computer readable medium can be coupled to the processor in order to store data used by the processor and other system elements. The processor interacts with the other components of the system as described more fully throughout the present specification. In an embodiment, the memory can include a look up table that can be utilized to control one or more components of the laser system surgery system.

The processor can be a general purpose microprocessor configured to execute instructions and data such as a processor manufactured by the Intel Corporation of Santa Clara, Calif. It can also be an Application Specific Integrated Circuit (ASIC) that embodies at least part of the instructions for performing the method according to the embodiments of the present disclosure in software, firmware and/or hardware. As an example, such processors include dedicated circuitry, ASICs, combinatorial logic, other programmable processors, combinations thereof, and the like.

The memory can be local or distributed as appropriate to the particular application. Memory can include a number of memories including a main random access memory (RAM) for storage of instructions and data during program execution and a read only memory (ROM) in which fixed instructions are stored. Thus, the memory provides persistent (non-volatile) storage for program and data files, and may include a hard disk drive, flash memory, a floppy disk drive along with associated removable media, a Compact Disk Read Only Memory (CD-ROM) drive, an optical drive, removable media cartridges, and other like storage media.

The user interface devices 74 can include any suitable user input/output device suitable to provide user input to the control electronics 70. For example, the user interface devices 74 can include devices such as a touch-screen display/input device, a keyboard, a footswitch, a keypad, a patient interface radio frequency identification (RFID) reader, an emergency stop button, a key switch, and so on.

Next, the characteristics of a cataract lens cut by the laser system 10 will be discussed. Received light is scattered by the clouding of a cataract lens. The higher the grade of the cataract, the more laser energy is needed to overcome the scattering and attenuation of the lens to deposit the beam energy at a desired location. Similarly, along an increasing depth of the cataract, the attenuation of beam energy will increase. For these reasons, a white cataract cannot be laser treated, but a semi-transparent cataract can be laser cut.

Increasing laser energy into a cataract lens may compensate for scattering losses at a given depth, but shallow layers of the lens are then treated with higher energy levels than desirable. For example, high laser energy deposition in grade 1-2 cataracts create large bubbles and high laser energy deposition in grade 2-4 cataracts propagate cracks in the lamellas. Therefore, simply increasing the energy level of a treatment beam into a lens will not improve lens fragmentation.

For sub-nanosecond laser systems, a sensitive range of energies are available to cut a cataract cleanly without cracking. If the energy applied is small, incomplete separation of tissue results. If the energy applied is high, then excess collateral damage in the tissue appears and subsequent laser pulses scatter due to an irregular refraction index change. Furthermore, excessive energy will slow down the fragmentation procedure due to a maximum safe power of treatment.

The methods and systems described herein improve the consistency and quality of a laser fragmentation cut by adjusting the treatment energy to match the dynamic range of energies needed to form consistent cuts at different depths of the tissue for sub-nanosecond/infrared/picosecond lasers. For instance, some embodiments include an infrared (e.g., 1 µs) laser assembly capable of performing both capsulotomy and lens fragmentation as described in detail below. This configuration further provides a cost-effective and efficient system where a single laser assembly is suitable for a plurality of surgical procedures.

Figure 3:
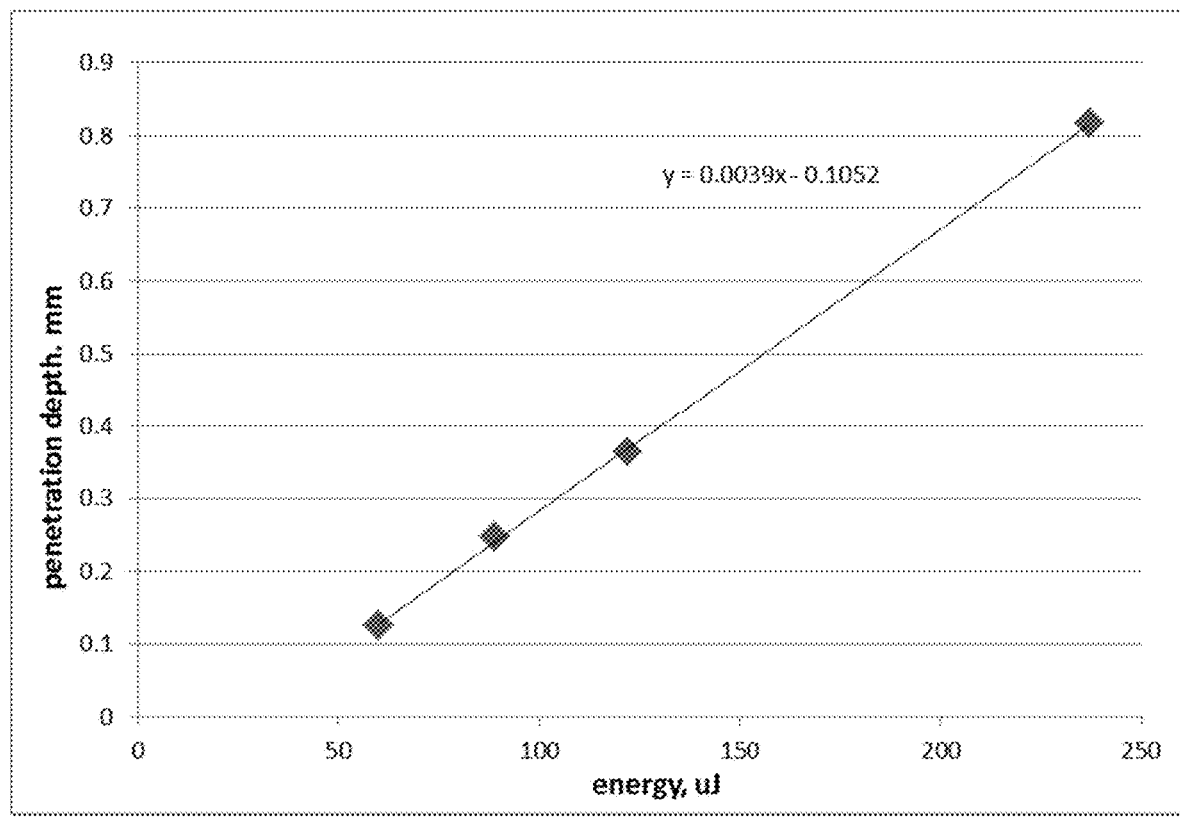
FIG. 3 is a graph illustrating penetration depth versus energy in a lens cut, in accordance with many embodiments.

FIG. 3 is a graph illustrating penetration depth versus energy in a lens cut, in accordance with many embodiments. The greater the energy applied to the tissue, the higher the penetration depth of the cut. Specifically, penetration depth scales linearly with the energy of the beam.

Figure 4:
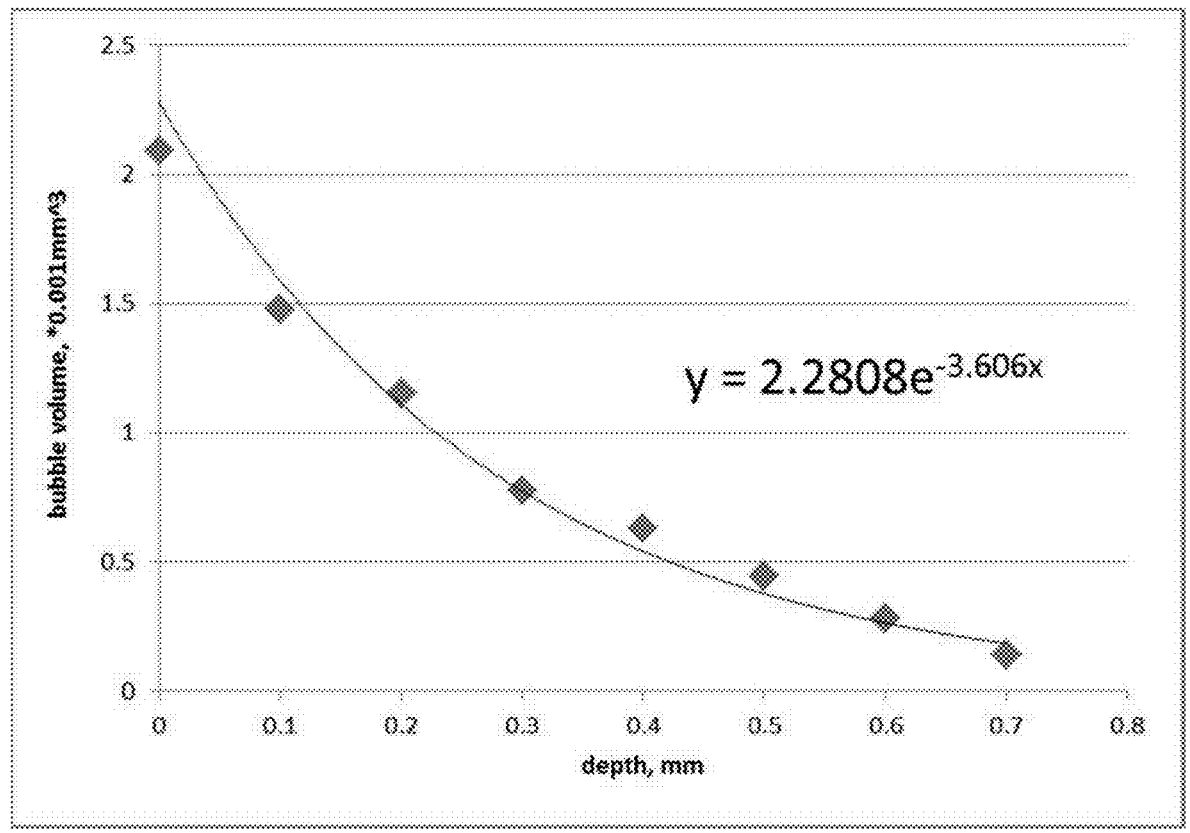
FIG. 4 is a graph illustrating bubble volume versus cut depth in a lens cut, in accordance with many embodiments.

FIG. 4 is a graph illustrating bubble volume versus cut depth in a lens cut, in accordance with many embodiments. A bubble volume measurement represents an intensity of local tissue treatment and it is assumed that the energy in the focal spot of a laser pulse is transferred into the mechanical energy of the bubble. FIG. 4 illustrates that along a depth of the lens, a bubble volume for a given energy level of a laser pulse decays exponentially. For a lens cut performed at a single energy, the consistency of the cut will vary continuously since the bubble volume decays exponentially. Therefore, maintaining a single energy level throughout a depth of the cut provides poor cut quality. The index of the exponent is a function of the initial energy. The bubble volume V may be expressed by the following equation 1:

$$V = V_o \exp\left[-\frac{xE_{th}}{x_o(E - E_{th})}\right] \quad \text{(eq. 1)}$$

Where $V_0$ is a bubble coefficient, $E_{th}$ is bubble threshold energy, E is the laser pulse energy, $x_0$ is penetration depth at $2E_{th}$, and x is the depth of the cut.

Accordingly, to provide a consistent and uniform laser fragmentation cut along a depth of a lens, a bubble volume should maintain the same size throughout an entire depth of the cut. Setting the bubble volume V as a constant value const, equation 1 may be reduced to equation 2:

$$\frac{xE_{th}}{x_o(E - E_{th})} = const \quad \text{(eq. 2)}$$

Solving for E provides for equation 3:

$$E = E_{th}\left[1 + \frac{x}{const\, x_o}\right] \quad \text{(eq. 3)}$$

Typically, the energy threshold $E_{th}$ and depth x are known values. The energy E may be preferably selected to be within a range of 2-10 times the threshold energy $E_{th}$ to achieve a bubble volume that provides a high quality lens cut. In a non-limiting example, if E is set $5E_{th}$, then const in equation 2 can be solved for. Then substituting the solved const into equation 3 results in equation 4:

$$E = E_{th}\left[1 + \frac{4x}{x_o}\right] \quad \text{(eq. 4)}$$

Equation 4 shows that the energy E of the beam increases linearly with increasing depth to maintain a uniform bubble volume. Conversely, for a lens fragmentation that begins at a bottom of lens, the energy E should decrease linearly as the cut depth decreases to maintain a uniform bubble volume and achieve a high quality cut.

Figure 5:
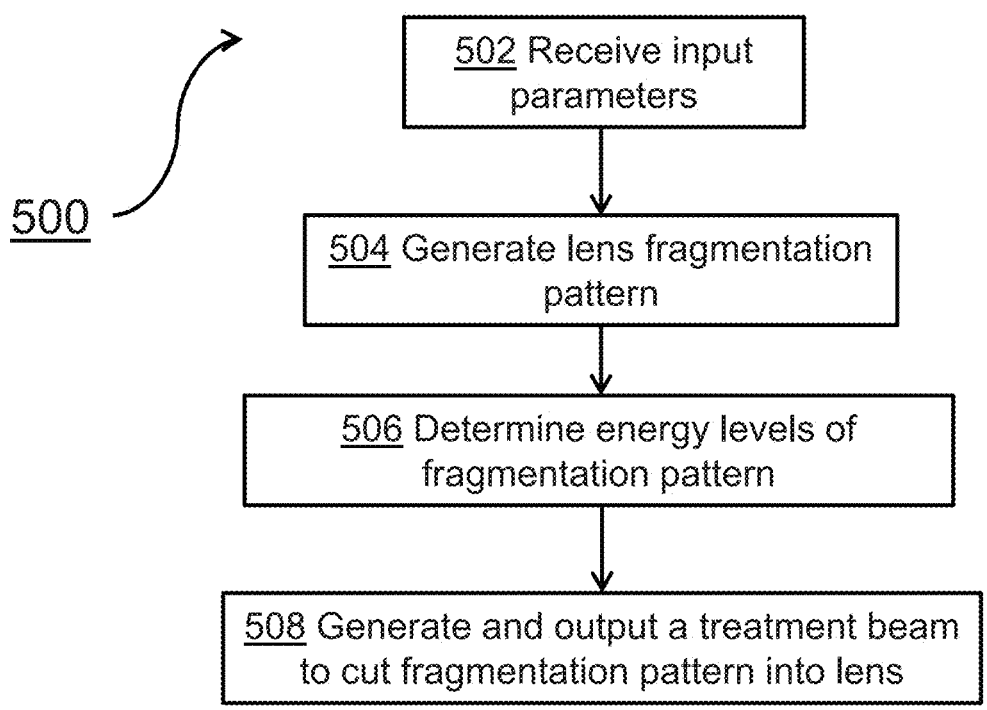
FIG. 5 shows a flowchart of a fragmentation pattern method of a lens, in accordance with many embodiments.

FIG. 5 shows a flowchart of a fragmentation pattern method 500 of a lens, in accordance with many embodiments. In the following non-limiting example, a laser beam trajectory is for lens fragmentation in cataract surgery. A laser cataract surgery system 10 is provided and includes a sub-nanosecond laser assembly 12 generating a treatment beam 28 that includes a plurality of laser beam pulses. The sub-nanosecond laser assembly 12 is, for example, a picosecond laser outputting a 150 picosecond treatment beam. The method 500 comprises the following main steps.

In step 502, the lens fragmentation process begins with reception of a plurality of input parameters. The trajectory may be computed based on fragmentation parameters including grid shape, depth, diameter, limited diameter (mm), segmentation/soft grid spacing (µm), diagnostic lens thickness (mm), spot spacing (µm), depth spacing (µm), number of cross replicates, lens anterior safe distance (µm), iris safe distance (µm), iris angle NA (deg), lens posterior safe distance (µm), pulse energy (µJ), average power (mW), and the like.

Selection of diagnostic thickness allows the user to input a previously measured lens thickness. The diameter parameter may be maximized to the diameter of the lens segmentation or limited so as to constrain the diameter of the lens segmentation. The grid shape parameter allows selection of quadrant, sextant, and octant cuts, for example. The grid spacing parameter defines the density of the grid. The segmentation/soft grid spacing parameter defines the separation of the grid from the center of the fragmentation pattern (e.g., the middle cross). The spot spacing parameter defines the distance between laser burn spots. Lens fragmentation is performed from the posterior to anterior of the lens. Therefore, the pulse energy is selected for the bottom of the cut. The pulse energy may preferably be selected to be a value between two to ten times the threshold energy in order to provide a cut without bridging or cracking. For example, the sub-nanosecond laser source may preferably generate the treatment beam with an energy five times the energy threshold of the tissue.

In step 504, the processor determines a lens cut fragmentation pattern that defines the laser trajectory of the lens segmentation treatment. The laser trajectory includes a set of positions and corresponding energies and is based on the received input parameters.

In step 506, the set of energy settings corresponding to the trajectory positions are determined by the processor. As discussed above, the energy of the treatment beam is adjusted to match a depth of the cut according to the above equations. Specifically, the energy increases linearly with increasing depth of the cut. The energies of the treatment beam are determined as a linear function of a depth of the lens cut pattern. Since the cut begins from a bottom of the lens, the energy of the treatment beam decreases as a function of the depth of the lens linearly from the posterior to the anterior of the lens. By scaling the treatment beam energy to a depth of the lens, a consistent bubble volume is maintained to ensure a high quality cut. Scattering coefficients at each depth may be extracted from OCT, confocal scanning or video images as described above. In step 508, the processor controls the system 10 to generate and output the treatment beam 28 according to the laser trajectory and corresponding energy settings to cut the fragmentation pattern into the lens. A treatment beam 28 is generated by the sub-nanosecond laser assembly 12 and includes a plurality of laser beam pulses. The treatment beam 28 is output according to the lens cut pattern of step 504 and energies of step 506.

The processor system may comprise tangible medium embodying instructions of a computer program to perform one or more of the method steps as described herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A laser cataract surgery system, comprising:
    a sub-nanosecond laser source generating a treatment beam that includes a plurality of laser beam pulses;
    an optical delivery system coupled to the sub-nanosecond laser source to receive and direct the treatment beam; and
    a processor coupled to the sub-nanosecond laser source and the optical delivery system, the processor comprising a tangible non-volatile computer readable medium comprising instructions to:
        determine a lens cut pattern inside a lens of an eye for lens fragmentation, the lens cut pattern including a plurality of trajectory positions each having a depth defined from an anterior surface of the lens;
        determine a plurality of pulse energies of the treatment beam to be delivered to the corresponding plurality of trajectory positions based on a linear function between the pulse energy of the treatment beam and the depth of the trajectory position; and
        control the sub-nanosecond laser source and the optical delivery system to deliver a plurality of focal points of laser pulses inside the lens of the eye to generate bubbles inside the lens at the focal points, wherein each laser pulse focal point is delivered to one of the plurality of trajectory positions at a corresponding depth inside the lens as defined by the cut pattern and has a corresponding one of the pulse energies, wherein the bubbles generated by the plurality of laser pulse focal points form cuts inside the lens.

2. The laser cataract system of claim 1, wherein the plurality of pulse energies of the treatment beam are between twice an energy threshold and ten times the energy threshold.

3. The laser cataract system of claim 2, wherein the energy threshold is an energy level at which visible damage in tissue is first observed.

4. The laser cataract system of claim 3, wherein the sub-nanosecond laser source generates the treatment beam with a pulse energy five times the energy threshold.

5. The laser cataract system of claim 1, wherein the sub-nanosecond laser source is a picosecond laser.

6. The laser cataract system of claim 1, wherein the sub-nanosecond laser generates a 150 picosecond treatment beam.

7. The laser cataract system of claim 1, further comprising: an image capture system for capturing an image of the eye.

8. The laser cataract system of claim 1, further comprising: a patient interface system to couple the eye with the optical delivery system so as to constrain the eye relative to the optical delivery system.

9. A method of fragmenting a lens of an eye, comprising:
generating a treatment beam that includes a plurality of laser beam pulses by a sub-nanosecond laser source;
determining a lens cut pattern inside the lens of the eye for lens fragmentation, the lens cut pattern including a plurality of trajectory positions each having a depth defined from an anterior surface of the lens;
determining a plurality of pulse energies of the treatment beam to be delivered to the corresponding plurality of trajectory positions based on a linear function between the pulse energy of the treatment beam and the depth of the trajectory position; and
controlling the sub-nanosecond laser source and an optical delivery system to deliver a plurality of focal points of laser pulses inside the lens of the eye to generate bubbles inside the lens at the focal points, wherein each laser pulse focal point is delivered to one of the plurality of trajectory positions at a corresponding depth inside the lens as defined by the cut pattern and has a corresponding one of the pulse energies, wherein the bubbles generated by the plurality of laser pulse focal points form cuts inside the lens.

10. The method of claim 9, wherein the plurality of pulse energies of the treatment beam are between twice an energy threshold and ten times an energy threshold.

11. The method of claim 10, wherein the pulse energy threshold is an energy level at which visible damage in tissue is first observed.

12. The method of claim 11, wherein the sub-nanosecond laser source generates the treatment beam with an energy five times the energy threshold of the tissue.

13. The method of claim 9, wherein the sub-nanosecond laser source is a picosecond laser.

14. The method of claim 9, wherein the sub-nanosecond laser generates a 150 picosecond treatment beam.

15. The method of claim 9, further comprising: capturing an image of the eye by an image capture system.

16. The method of claim 9, further comprising: coupling the eye with the optical delivery system so as to constrain the eye relative to the optical delivery system by a patient interface system.

17. The method of claim 9, wherein the plurality of laser pulses are delivered to the lens starting from a bottom of the lens.

18. A method of fragmenting a lens of an eye, comprising:
generating a treatment beam that includes a plurality of laser beam pulses by a sub-nanosecond laser source;
determining a lens cut pattern inside the lens of the eye for lens fragmentation, the lens cut pattern including a plurality of trajectory positions each having a depth defined from an anterior surface of the lens;
determining a plurality of pulse energies of the treatment beam to be delivered to the corresponding plurality of trajectory positions based on a relationship among a bubble volume of a bubble generated by a treatment beam, the pulse energy of the treatment bean, and the depth of the trajectory position, wherein the determined plurality of pulse energies maintain a constant bubble volume at all of the plurality of trajectory positions; and
controlling the sub-nanosecond laser source and an optical delivery system to deliver a plurality of focal points of laser pulses inside the lens of the eye, wherein each laser pulse focal point is delivered to one of the plurality of trajectory positions at a corresponding depth inside the lens as defined by the cut pattern and has a corresponding one of the pulse energies, wherein the plurality of laser pulse focal points form cuts inside the lens.

19. The method of claim 18, wherein the pulse energy increases linearly with the depth of the trajectory position.

20. The method of claim 18, wherein the plurality of laser pulses are delivered to the lens starting from a bottom of the lens.

* * * * *